US012576060B2

(12) United States Patent
Gokaraju et al.

(10) Patent No.: US 12,576,060 B2
(45) Date of Patent: Mar. 17, 2026

(54) WATER SOLUBLE 3-O-ACETYL-11-KETO-β-BOSWELLIC ACID AND METAL ION COMPOSITIONS, PROCESS FOR THEIR PREPARATION AND USES THEREOF

(71) Applicant: LAILA NUTRA PRIVATE LIMITED, Vijayawada (IN)

(72) Inventors: Ganga Raju Gokaraju, Vijayawada (IN); Rama Raju Gokaraju, Vijayawada (IN); Trimurtulu Golakoti, Vijayawada (IN); Venkata Kanaka Ranga Raju Gokaraju, Vijayawada (IN); Kiran Bhupathiraju, Vijayawada (IN); Venkata Krishna Raju Alluri, Vijayawada (IN); Venkateswarlu Somepalli, Vijayawada (IN); Krishanu Senguptha, Vijayawada (IN); Seth Noah Flowerman, New York, NY (US)

(73) Assignee: Laila Nutra Private Limited, Vijayawada (IN)

( * ) Notice: Subject to any disclaimer, the term of this patent is extended or adjusted under 35 U.S.C. 154(b) by 635 days.

(21) Appl. No.: 18/012,411

(22) PCT Filed: Jun. 23, 2021

(86) PCT No.: PCT/IN2021/050609

§ 371 (c)(1),
(2) Date: Dec. 22, 2022

(87) PCT Pub. No.: WO2021/260731

PCT Pub. Date: Dec. 30, 2021

(65) Prior Publication Data

US 2023/0346736 A1 Nov. 2, 2023

(30) Foreign Application Priority Data

Jun. 23, 2020 (IN) ............................ 202041021739

(51) Int. Cl.
*A61K 31/22* (2006.01)
*A61K 33/00* (2006.01)
*A61P 21/00* (2006.01)

(52) U.S. Cl.
CPC .............. *A61K 31/22* (2013.01); *A61K 33/00* (2013.01); *A61P 21/00* (2018.01)

(58) Field of Classification Search
CPC ..................................................... A61K 31/22
See application file for complete search history.

(56) References Cited

U.S. PATENT DOCUMENTS

| | | | | |
|---|---|---|---|---|
| 6,949,260 | B2 | 9/2005 | Krumhar | |
| 8,563,047 | B2 | 10/2013 | Arent | |
| 2003/0185907 | A1 | 10/2003 | Krumhar | |
| 2004/0166178 | A1 | 8/2004 | Meybeck et al. | |
| 2011/0052750 | A1 | 3/2011 | Rietjens et al. | |
| 2013/0116211 | A1 | 5/2013 | Gokaraju et al. | |
| 2016/0030498 | A1 * | 2/2016 | Shapeti ................ | A61K 36/487 424/769 |
| 2017/0224659 | A1 | 8/2017 | Bijno et al. | |

FOREIGN PATENT DOCUMENTS

| | | |
|---|---|---|
| CN | 103193852 | 7/2013 |
| CN | 103193853 | 7/2013 |
| EP | 3506891 | 7/2019 |
| WO | WO2011061292 | 5/2011 |

OTHER PUBLICATIONS

Azeemuddin et al. "Pharmacological investigation of 'HlM-CHX': A herbal combination in the experimental muscle wasting condition", Experimental Gerontology, 125 (2019), 10 pages
European Search Report and Written Opinion for EP 21827843.0, dated Jul. 9, 2024, 10 pages
Gupta et al., "Salts of Therapeutic Agents: Chemical, Physicochemical, and Biological Considerations", Molecules, 2018, 23, 1719, 15 pages.
International Search Report and Written Opinion for PCT/IN2021/050609, dated Oct. 19, 2021, 9 pages.
National Library of Medicine, National Center for Biotechnology Information, "Substance Record" SID 170476309, Acetyl-11-keto-beta-boswellic acid sodium salt, Dec. 16, 2013, 5 pages.
National Library of Medicine, National Center for Biotechnology Information, "Substance Record" SID 170488516, Acetyl-11-keto-beta-boswellic acid potassium salt, Dec. 23, 2013, 5 pages.
Serajuddin, "Salt formation to improve drug solubility", Advanced Drug Delivery Reviews, 59 (2007), pp. 603-616.

* cited by examiner

*Primary Examiner* — Rei Tsang Shiao
(74) *Attorney, Agent, or Firm* — Dority & Manning, P.A.

(57) ABSTRACT

The present invention discloses water-soluble 3-O-acetyl-11-keto-β-boswellic acid compositions comprising 3-O-acetyl-11-keto-β-boswellic acid in combination with a metal ion selected from potassium or sodium in the form of respective metal salt or complex or chelate; process for their preparation; methods of prevention, control and/or treatment of at least one disorder selected from muscle soreness, delayed-onset of muscle soreness (DOMS), muscles tenderness, muscle pain, muscle fatigue, muscle sprain, temporary loss of muscle strength and swelling in muscles.

23 Claims, No Drawings

WATER SOLUBLE 3-O-ACETYL-11-KETO-β-BOSWELLIC ACID AND METAL ION COMPOSITIONS, PROCESS FOR THEIR PREPARATION AND USES THEREOF

TECHNICAL FIELD OF THE INVENTION

The present invention relates to water-soluble 3-O-acetyl-11-keto-β-boswellic acid compositions comprising 3-O-acetyl-11-keto-β-boswellic acid in combination with a metal ion selected from potassium or sodium in the form of respective metal salt or complex or chelate; for prevention, control and/or treatment of at least one disorder/condition selected from muscle soreness, delayed-onset of muscle soreness (DOMS), muscles tenderness, muscle pain, muscle fatigue, muscle sprain, temporary loss of muscle strength and swelling in muscles.

BACKGROUND OF THE INVENTION

Muscle soreness is the aching and stiffness resulted from the stress put on muscles during exercise. Acute muscle soreness is the pain or burning sensation felt in muscle during or immediately after a workout, which is due to a quick build-up of lactic acid. Delayed-onset muscle soreness (DOMS) is the second type of muscle soreness that begins sometime after a body workout. DOMS usually begins within 6-8 hours after unfamiliar sporting activities or eccentric exercise or a change in activity, and can peak at 24-48 hours and lasts up to 72 hours after the exercise.

*Boswellia* resin and its extracts have been in use for the treatment of inflammatory diseases for ages. Boswellic acids were identified as the active compounds responsible for the anti-inflammatory activity of the resin. 3-O-acetyl-11-keto-β-boswellic acid (AKBA), a minor compound in resin is the most potent of all the boswellic acids in inhibiting 5-lipoxygenase (E. R. Sailor et al., British J. Pharmacology, 1996, 117, 615-618). Many processes for producing AKBA from *Boswellia serrata* extracts were disclosed in known art. The chemical structure of AKBA is shown below.

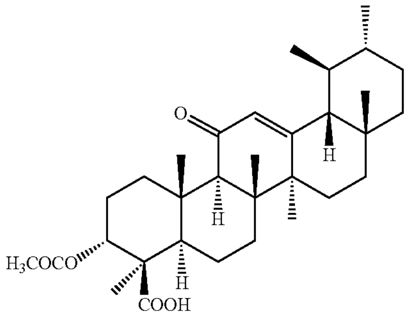

Chemical structure of AKBA

3-O-acetyl-11-keto-β-boswellic acid is a lipophilic triterpenoid and is poorly soluble in water. As such, it has limited therapeutic applications in its natural form for the prevention, control, and treatment of various diseases and health conditions.

Many synthetic non-steroid anti-inflammatory drugs (NSAIDs) are commercially available, but they are known to cause some side effects. Hence, there is a continuous need in the art to provide highly potent alternative treatments comprising highly effective herbal compounds for preventing, treating, or controlling muscle soreness, muscles tenderness, muscle pain, muscle fatigue, muscle sprain, temporary loss of muscle strength, and swelling in muscles, osteoarthritis, rheumatoid arthritis, and asthma. There are few herbal compositions available in the literature for treating pain and inflammation, as discussed below.

U.S. Pat. No. 6,949,260B2 disclosed a method of treating an ailment involving pain and inflammation in a mammal comprising administering to the mammal a composition comprising, in parts by weight, about 10 to 1800 parts of *Boswellia* gum extract comprising at least 10% by weight of boswellic acids, and about 50 to 400 parts of turmeric gum extract comprising at least about 30% by weight of curcuminoids. Wherein the ailment is selected from the group consisting of rheumatoid arthritis, osteoarthritis, juvenile rheumatoid arthritis, gout, low back pain, minor soft tissue injury, minor burn, sprain, headache, general muscle soreness, swelling, stiffness, and chronic inflammatory disease.

Another patent, U.S. Pat. No. 8,563,047B2, disclosed a method for treating a human suffering from delayed onset muscle soreness as a result of exercise. Essentially, the method consisted of administering an amount of an extract of black tea or oolong tea effective to treat said human suffering from delayed onset muscle soreness, wherein the extract is selected from the group consisting of an ethyl acetate extract, an ethanol extract, and a super critical $CO_2$ extract.

US2011052750A1 disclosed a nutraceutical composition comprising olive extract, which is effective in promoting muscle health in an animal, including humans, which is subject to post-exercise muscle soreness, muscle pain, or muscle injury due to lactic acid accumulation.

EP3506891A1 discloses a *capsicum* composition that enhances resistance to fatigue by enhancing the oxidative capacity of the muscles through the reduction in muscle soreness and enhancing post-exercise recovery from muscle fatigue when administered in an effective amount to the subject undergoing physical activity.

Despite the availability of various herbal compositions, there remains a need in the art for better and cost-effective treatment options with minimal side effects, thereby making the option safe for human consumption especially when used in long-term therapy with minimal or no side effects.

OBJECT OF THE INVENTION

Therefore, the primary object of the invention is to provide water-soluble 3-O-acetyl-11-keto-β-boswellic acid compositions comprising 3-O-acetyl-11-keto-β-boswellic acid in combination with a metal ion selected from potassium or sodium in the form of respective metal salt or complex or chelate; for prevention, control and/or treatment of at least one disorder/condition selected from muscle soreness, delayed-onset of muscle soreness (DOMS), muscles tenderness, muscle pain, muscle fatigue, muscle sprain, temporary loss of muscle strength and swelling in muscles.

Another object of the invention is to provide a process for the preparation of 3-O-acetyl-11-keto-β-boswellic acid compositions comprising 3-O-acetyl-11-keto-β-boswellic acid in combination with a metal ion selected from potassium or sodium in the form of respective metal salt or complex or chelate.

Yet another object of the invention is to provide methods of prevention, control and/or treatment of at least one disorder selected from muscle soreness, delayed-onset of muscle soreness (DOMS), muscles tenderness, muscle pain, muscle fatigue, muscle sprain, temporary loss of muscle strength and swelling in muscles in humans, wherein the method comprises supplementing the said human with a water-soluble composition comprising 3-O-acetyl-11-keto-β-boswellic acid in combination with a metal ion selected from potassium or sodium in the form of respective metal salt or complex or chelate; and optionally containing at least one component selected from pharmaceutically or nutraceutically or dietetically acceptable excipients, carriers or diluents.

SUMMARY OF THE INVENTION

The present invention provides water-soluble 3-O-acetyl-11-keto-β-boswellic acid compositions comprising 3-O-acetyl-11-keto-β-boswellic acid in combination with a metal ion selected from potassium or sodium in the form of respective metal salt or complex or chelate; for prevention, control and/or treatment of at least one disorder selected from muscle soreness, delayed-onset of muscle soreness (DOMS), muscles tenderness, muscle pain, muscle fatigue, muscle sprain, temporary loss of muscle strength and swelling in muscles.

The present invention provides water-soluble 3-O-acetyl-11-keto-β-boswellic acid compositions comprising 3-O-acetyl-11-keto-β-boswellic acid in combination with a metal ion selected from potassium or sodium in the form of respective metal salt or complexor chelate; and optionally containing at least one component selected from pharmaceutically or nutraceutically or dietetically acceptable excipients, carriers or diluents; for prevention, control and/or treatment of at least one disorder selected from muscle soreness, delayed-onset of muscle soreness (DOMS), muscles tenderness, muscle pain, muscle fatigue, muscle sprain, temporary loss of muscle strength and swelling in muscles.

One aspect of the present invention provides a process for the preparation of the compositions comprising 3-O-acetyl-11-keto-β-boswellic acid in combination with a metal selected from potassium or sodium in the form of respective metal salt or complex or chelate.

Other aspect of the invention provides methods of prevention, control and/or treatment of at least one disorder/condition selected from muscle soreness, delayed-onset of muscle soreness (DOMS), muscles tenderness, muscle pain, muscle fatigue, muscle sprain, temporary loss of muscle strength and swelling in muscles in humans, wherein the method comprises supplementing said human with water-soluble 3-O-acetyl-11-keto-β-boswellic acid compositions comprising 3-O-acetyl-11-keto-β-boswellic acid in combination with a metal ion selected from potassium or sodium in the form of respective metal salt or complex or chelate; and optionally containing at least one component selected from pharmaceutically or nutraceutically or dietetically acceptable excipients, carriers or diluents.

Yet another object of the invention provides the use of water-soluble 3-O-acetyl-11-keto-β-boswellic acid compositions comprising 3-O-acetyl-11-keto-β-boswellic acid in combination with a metal ion selected from potassium or sodium in the form of respective metal salt or complex or chelate; and optionally containing at least one component selected from pharmaceutically or nutraceutically or dietetically acceptable excipients, carriers or diluents; for prevention, control and/or treatment of at least one disorder selected from muscle soreness, delayed-onset of muscle soreness (DOMS), muscles tenderness, muscle pain, muscle fatigue, muscle sprain, temporary loss of muscle strength and swelling in muscles.

DETAILED DESCRIPTION OF THE INVENTION

The invention will now be described in detail in connection with certain preferred and optional embodiments so that various aspects thereof may be more fully understood and appreciated.

Potassium and sodium are inorganic substances required by the body in small amounts for various biological functions. Sodium is the primary cation in animals and humans. Sodium plays a key role in the regulation of blood volume, blood pressure, osmotic balance, and maintains a constant pH. A daily supplementation between 115 and 500 mg is required depending on sweating due to physical activity or adaptation to the climate. Sodium chloride is the principal source of sodium in the diet. Potassium is the essential mineral needed in higher quantity than any other metal, with a requirement of up to 3500 mg per day. Potassium plays a vital role in blood pressure regulation, carbohydrate metabolism, and fluid balance. The functions of potassium and sodium in living organisms are quite different. Potassium is the major cation present inside the animal cells, while sodium is the major cation present outside the animal cells, and they play a critical role in creating membrane potential 3-O-acetyl-11-keto-β-boswellic acid (AKBA) is a very potent natural molecule for different health applications, but is very poorly soluble in water. Hence, its health benefits are severely limited.

The inventors presumed that the potassium or sodium salts or metal ion complexes of 3-O-acetyl-11-keto-β-boswellic acid would increase water solubility, and result in improved bio-availability; and thereby increase their therapeutic applications such as alleviating muscle soreness, muscle pain, muscle fatigue, muscle sprain, temporary loss of muscle strength and swelling in muscles.

Thus, in view of these potential benefits, the inventors of the present invention prepared several compositions comprising 3-O-acetyl-11-keto-β-boswellic acid in combination with a metal ion selected from potassium or sodium as the respective metal salt or complex or chelate as depicted below.

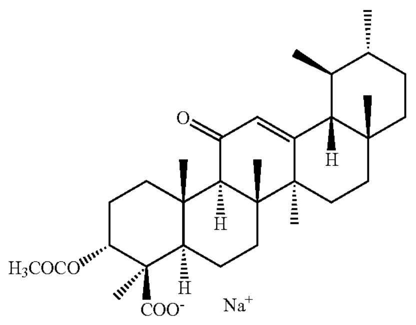

Sodium salt of AKBA

-continued

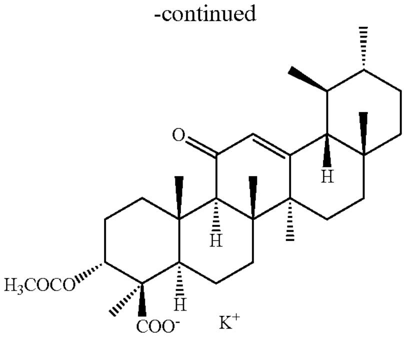

Potassium salt of AKBA

As referred herein at various instances in the specification, 3-O-acetyl-11-keto-β-boswellic acid salts, chelates, or complexes are the product formed by the treatment of 3-O-acetyl-11-keto-β-boswellic acid with a metal compound. The metal compound is selected from the salts, hydroxides, oxide, and carbonates of potassium or sodium.

The inventive water-soluble 3-O-acetyl-11-keto-β-boswellic acid compositions comprising 3-O-acetyl-11-keto-β-boswellic acid in combination with a metal selected from potassium or sodium as the respective metal salt or complex or chelate; wherein the 3-O-acetyl-11-keto-β-boswellic acid is in the range of 30-95% and potassium or sodium is in the range of 3.0-10%.

For example, 3-O-acetyl-11-keto-β-boswellic acid having upto 99% purity by HPLC (LN04) prepared from *Boswellia serrata* gum resin was dissolved in methanol, and the solution was treated with potassium hydroxide to form potassium salt or complex or chelate of 3-O-acetyl-11-keto-β-boswellic acid (LN05). The product was estimated for its 3-O-acetyl-11-keto-β-boswellic acid by HPLC and potassium by Flame photometry and found that it contains 90.85% of 3-O-acetyl-11-keto-β-boswellic acid and 6.46% of potassium. Similarly, treatment of a methanolic solution of LN04 with sodium hydroxide forms sodium salt of 3-O-acetyl-11-keto-β-boswellic acid (LN06). The product contains 90.33% of 3-O-acetyl-11-keto-β-boswellic acid and 4.56% of sodium.

In another example, 3-O-acetyl-11-keto-β-boswellic acid having upto 90% purity by HPLC (LN03) prepared from *Boswellia serrata* gum resin was dissolved in methanol, and the solution was treated with potassium hydroxide to form potassium salt or complex or chelate of 3-O-acetyl-11-keto-β-boswellic acid (LN07). The product was estimated for its 3-O-acetyl-11-keto-β-boswellic acid by HPLC and potassium by Flame photometry and found that it contains 80.77% of 3-O-acetyl-11-keto-β-boswellic acid and 6.55% of potassium. Similarly, treatment of methanolic solution of LN03 with sodium hydroxide forms sodium salt of 3-O-acetyl-11-keto-β-boswellic acid (LN08). The product was found to contain 82.16% of 3-O-acetyl-11-keto-β-boswellic acid and 4.68% of sodium.

Similarly, 3-O-acetyl-11-keto-β-boswellic acid having upto 60% purity by HPLC (LN02) and upto 40% purity by HPLC (LN01) prepared from *Boswellia serrata* gum resin were dissolved separately in methanol, and these solutions were treated with required concentrations of potassium hydroxide to form potassium salt or complex or chelate of 3-O-acetyl-11-keto-β-boswellic acid (LN09) and potassium salt or complex or chelate of 3-O-acetyl-11-keto-β-boswellic acid (LN10) respectively and results were depicted in Table-1.

Surprisingly, the inventors found that the metal salts or complexes or chelates of 3-O-acetyl-11-keto-β-boswellic acid are completely water-soluble, whereas the starting materials, i.e. AKBA compounds with different purities are not water-soluble, and the solubility data was presented in table-2.

For example, 1.0 g of 99% AKBA (LN04) was not completely soluble even in 1000 mL of water, whereas 1.0 g of its K salt containing 90% AKBA (LN05) prepared from LN04 was completely soluble in 140 mL of water at room temperature (RT). The other salts of AKBA (LN06-LN09) were also completely soluble in water, and the data was presented in Table-2.

The present invention also provides a process for the preparation of water-soluble 3-O-acetyl-11-keto-β-boswellic acid compositions comprising 3-O-acetyl-11-keto-β-boswellic acid in combination with a metal ion selected from potassium or sodium as the respective metal salt or complex or chelate.

Thus, the process for the preparation of water-soluble 3-O-acetyl-11-keto-β-boswellic acid compositions comprises the following steps;

(i) dissolving 3-O-acetyl-11-keto-β-boswellic acid in a suitable solvent;
(ii) treating the solution with a metal compound;
(iii) filtering the solution; and
(iv) evaporating the solvent and drying the residue to obtain the corresponding metal salt or chelate or complex of 3-O-acetyl-11-keto-β-boswellic acid.

The suitable solvent used in the process for the preparation of 3-O-acetyl-11-keto-β-boswellic acid compositions according to the present invention is selected from but not limited to C1-C5 alcohols, like ethanol, methanol, propanol, n-butanol and mixtures thereof.

The metal compound used in the process for the preparation of 3-O-acetyl-11-keto-β-boswellic acid compositions is selected from the metal salts, metal oxides, metal hydroxides, or carbonates corresponding to a metal selected from potassium or sodium.

Formulations: The present invention also provides water-soluble 3-O-acetyl-11-keto-β-boswellic acid compositions comprising 3-O-acetyl-11-keto-β-boswellic acid in combination with a metal ion selected from potassium or sodium as the respective metal salt or complex or chelate, formulated into a dosage form selected from dry powder form, liquid form, beverage, food product, dietary supplement, or any suitable form such as a tablet, a capsule, or a soft chewable or gummy bear by using a at least one component selected from pharmaceutically or nutraceutically or dietetically acceptable excipients, carriers or diluents.

The water soluble 3-O-acetyl-11-keto-β-boswellic acid compositions comprising 3-O-acetyl-11-keto-β-boswellic acid in combination with a metal selected from potassium or sodium as the respective metal salt or complex or chelate; and optionally containing at least one component selected from pharmaceutically or nutraceutically or dietically acceptable excipients, carriers or diluents; for prevention, control and/or treatment of at least one disorder selected from muscle soreness, delayed-onset of muscle soreness (DOMS), muscles tenderness, muscle pain, muscle fatigue, muscle sprain, temporary loss of muscle strength and swelling in muscles; wherein the pharmaceutically or nutraceutically or dietically acceptable excipients, carriers and diluents are selected from Monosaccharide's such as glucose, dextrose, fructose, galactose etc.; Disaccharides such as but not limited to sucrose, maltose, lactose, lactulose, trehalose cellobiose, chitobiose etc.; Polycarbohydrates such as starch and modified starch such as sodium starch glycolate, pre-gelatinized starch, soluble starch, and other modified starches; Dextrins that are produced by hydrolysis of starch or glycogen such as yellow dextrin, white dextrin, maltodextrin etc.; Polyhydric alcohols or sugar alcohols such as but not limited to sorbitol, mannitol, inositol, xylitol, isomalt etc.; cellulose based derivatives such as but not limited to microcrystalline cellulose, hydroxy propyl methyl cellulose, hydroxy ethyl cellulose etc.; silicates such as but not limited to neusilin, veegum, talc, colloidal silicon dioxide etc.; metallic stearates such as but not limited to calcium stearate, magnesium stearate, zinc stearate etc.; Organic acids such as citric acid, tartaric acid, malic acid, succinic acid, lactic acid, L-ascorbic acid etc.; Fatty acid esters and esters of poly sorbate, natural gums such as but not limited to acacia, carrageenan, guar gum, xanthan gum etc.; vitamin B group, nicotinamide, calcium pantothenate, amino acids, proteins such as but not limited to casein, gelatin, pectin, agar; organic metal salts such as but not limited to sodium chloride, calcium chloride, dicalcium phosphate, zinc sulphate, zinc chloride etc.; natural pigments, flavors, class I & class II preservatives and aqueous, alcoholic, hydro-alcoholic, organic solutions of above listed ingredients alone or in combination.

Muscle soreness and DOMS. Muscle soreness is an offshoot of the stress put on muscles during a workout. Two types of muscle soreness are commonly known. Acute muscle soreness is the pain, or burning sensation felt in muscle during or immediately after a workout, which is due to a quick build-up of lactic acid. It usually disappears as soon as or shortly after stopping the exercise.

Delayed-Onset Muscle Soreness (DOMS) is the second type of muscle pain that begins sometime after a workout. According to the American College of Sports Medicine, DOMS symptoms typically appear at least 12 to 24 hours after a workout. The pain tends to peak at about one to three days, followed by a gradual recovery.

DOMS occurs after one or more of the following reasons. (i) starting an exercise or workout program for the very first time and (ii) adding a new activity or exercise to a regular workout program. Increasing the intensity of an exercise over and above the regular program, such as increasing the amount of weight lifted, number of repetitions, or speed. Repetition of the regular exercise activity without sufficient rest break in-between. High-intensity exercises such as eccentric exercises can cause tiny, microscopic tears in muscle fibers, which may lead to a delayed onset of soreness in the muscles. Eccentric exercises are movements that not only lengthen muscle but also under tension causes DOMS.

The main symptoms of DOMS include muscle tenderness, muscle pain, muscle fatigue, temporary loss of muscle strength, and swelling in muscles, which leads to reduced body flexibility and muscle stiffness when moving. Persons with DOMS are unable to carry out their regular daily activities related to living or working. This leads to loss of work hours and compromised quality of life.

The pathophysiology of DOMS/muscle soreness is thought to be muscle damage due to disruption of muscle fibrils. They are known to be triggered by a sequence of biochemical changes after muscle damage rather than a single event of damage. Inflammatory responses will occur only after the morphological damages caused by eccentric contractions. The increased levels of Leukotriene B4 (LTB4) and Prostaglandin $E_2$ ($PGE_2$) at the damaged site are implicated in the pain-related DOMS/muscle soreness. Hence, one of the strategies for alleviating the symptoms of DOMS can be regulating the LTB4 and $PGE_2$ levels.

The inventors of the current application screened the compositions comprising AKBA salts/chelates/complexes for their LTB4 inhibitory activities.

Leukotriene B4: Leukotriene B4 (LTB4) is a pro-inflammatory lipid mediator synthesized from arachidonic acid via activation of 5-lipoxygenase (5-LOX). LTB4 is one of the potent mediators of inflammation, causing increased activation, recruitment, migration, and adhesion of immune cells. Studies have shown that the LTB4 level is higher in the joints of osteoarthritis (OA) patients compared to the levels in healthy individuals. Increased synthesis of LTB4 plays a pathogenic role that contributes to the pain and inflammation in OA joints. Reduction of LTB4 is one of the promising strategies to alleviate inflammation and pain in OA.

Interestingly, these compositions comprising AKBA salts/chelates/complexes derived from enriched AKBA extracts from *Boswellia serrata* showed greater reductions of LTB4 productions than the enriched AKBA.

For example, 99% AKBA (without salt, LN04) showed 16.03% and 28.71% reduction in LTB4, at 1.0 μg/mL and 2.5 μg/mL respectively. The potassium salt containing 90% AKBA (LN05) produced from LN04 and potassium hydroxide showed better efficacy with 21.95% and 57.57% reductions of LTB4 respectively at 1.0 μg/mL and 2.5 μg/mL. These inhibitions are significantly higher compared to the corresponding AKBA compound (LN04). This is a surprising result. Similarly, the sodium salt containing 90% AKBA (LN06) produced from LN04 and sodium hydroxide showed 20.16% and 47.97% reductions of LTB4 at 1.0 μg/mL and 2.5 μg/mL respectively. These reductions are also significantly higher than those produced by LN04, suggesting a surprisingly higher efficacy for metal salts or complexes or chelates than the corresponding AKBA compound without salt form, as summarized in Table-3.

In another example, 90% AKBA (without salt, LN03) showed 16.72% and 26.83% reductions of LTB4 at 1.0 μg/mL and 2.5 μg/mL, respectively, whereas the potassium salt (LN07) containing 80% AKBA produced from LN03 and potassium hydroxide showed 20.26% and 55.85% reductions at 1.0 μg/mL and 2.5 μg/mL, respectively, which are significantly higher than those exhibited by LN03, suggesting a surprisingly higher efficacy than those shown by the corresponding AKBA compound without the salt form. Similarly, the sodium salt (LN08) containing 80% AKBA produced from LN03 and sodium hydroxide showed 21.66% and 46.10% reductions at 1.0 μg/mL and 2.5 μg/mL, respectively. These reductions are significantly higher than those shown by LN03, suggesting a surprisingly higher efficacy for metal salts or complexes or chelates than the corresponding AKBA compound without salt form as summarized in Table-4.

In another example, 60% AKBA (LN02) showed 10.85% and 22.05% reductions of LTB4 at 1.0 μg/mL and 2.5 μg/mL, respectively, whereas the potassium salt (LN09) containing 50% AKBA produced from LN02 showed 15.98% and 45.70% reductions of LTB4 at 1.0 μg/mL and 2.5 μg/mL, respectively. These reductions are significantly higher than those exhibited by LN02, suggesting a surprising improvement in efficacy compared to that shown by corresponding the AKBA without the salt form. Similarly, 40% AKBA (without salt, LN01) showed 9.57% and 18.40% reductions of LTB4 at 1.0 μg/mL and 2.5 μg/mL, respectively, whereas the potassium salt (LN10, 30% AKBA) produced from LN01 and potassium hydroxide showed 14.89% and 42.09% reductions of LTB4 at 1.0 μg/mL and 2.5 μg/mL, respectively. The reductions are significantly higher than those shown by the LN01, suggesting a surprisingly higher efficacy for metal salts or complexes or chelates than the corresponding AKBA compound without the salt form as summarized in Table-5.

The inventors of the current application screened the compositions comprising AKBA salts/chelates/complexes for their $PGE_2$ inhibitory activities.

Prostaglandin $E_2$ ($PGE_2$): Prostaglandins (PGs) are derived from arachidonic acid, which is released from lipid membranes by phospholipase A2 enzyme activation. Cyclooxygenase-2 (COX-2) is the key enzyme in prostaglandin $E_2$ or $PGE_2$ synthesis during inflammation. In inflammatory joints or OA, the $PGE_2$ level is remarkably elevated in the synovial fluid. $PGE_2$ increases the sensitivity of peripheral nociceptive primary afferent neurons and central nociceptive neurons, hence, contributes to the chronic disabling pain in arthritic joints. $PGE_2$ also contributes to synovial inflammation in OA by increasing local blood flow and potentiates the effects of bradykinin and interleukin (IL)-1β to induce vascular permeability. Hence, $PGE_2$ inhibition is an effective strategy to relieve pain and inflammation in muscles such as muscle soreness, delayed-onset of muscle soreness (DOMS), muscle tenderness, muscle pain, muscle fatigue, muscle sprain, temporary loss of muscle strength, and swelling in muscles.

Interestingly, the present compositions comprising AKBA salts/chelates/complexes derived from enriched AKBA extracts from *Boswellia serrata* showed greater reduction of $PGE_2$ production than the enriched AKBA.

For example, the 99% AKBA (LN04) showed 17.22% and 20.03% reductions of $PGE_2$ at 1.0 μg/mL and 2.5 μg/mL, respectively. Interestingly, the potassium salt (LN05) of LN4 containing 90% AKBA produced on treatment with potassium hydroxide showed 24.42% and 42.29% reductions of $PGE_2$ at 1.0 μg/mL and 2.5 μg/mL, respectively, which are significantly higher than those shown by LN04, suggesting a surprisingly higher efficacy for metal salts or complexes or chelates than corresponding AKBA compound. Similarly, sodium salt (LN06) containing 90% AKBA produced from LN04 and sodium hydroxide showed 25.64% and 41.23% reductions of $PGE_2$ at 1.0 μg/mL and 2.5 μg/mL, respectively. These reductions are significantly higher than those shown by LN04, suggesting a surprisingly higher efficacy for metal salts or complexes or chelates than the corresponding AKBA compound without salt, as summarized in Table-6.

In another example, the 90% AKBA (without salt, LN03) showed 15.02% and 26.28% reductions of $PGE_2$ at 1.0 μg/mL and 2.5 μg/mL, respectively. The potassium salt (LN07) containing 80% AKBA derived from LN03 on treatment with potassium hydroxide in comparison showed 26.50% and 49.08% reductions respectively at 1.0 μg/mL and 2.5 μg/mL., which are significantly higher than those shown by LN03, suggesting a surprisingly higher efficacy for metal salts or complexes or chelates compared to the corresponding AKBA free acid. Similarly, the sodium salt containing 80% AKBA (LN08) produced from LN03 and sodium hydroxide showed 25.61% and 47.56% reductions of $PGE_2$ at 1.0 μg/mL and 2.5 μg/mL, respectively. These reductions are significantly higher than those shown by LN03, suggesting a surprisingly higher efficacy for metal salts or complexes or chelates when compared to the corresponding AKBA free acid (LN03), as summarized in Table-7. Similarly, in other examples, the potassium salt (LN09) of LN02 containing 50% AKBA and potassium salt (LN10) of LN01 containing 30% AKBA both produced on treatment with potassium hydroxide also showed significantly higher reductions of $PGE_2$ than their corresponding AKBA compounds without the salt forms as summarized in Table-8.

C-reactive protein (CRP) and Delayed onset of muscle soreness (DOMS): Delayed onset muscle soreness (DOMS) is the sensation of muscular discomfort, painful, tender muscles during active contractions that occur in a delayed fashion after strenuous exercise. The pathophysiology of DOMS remains still undetermined, but it has been reported that after strenuous exercise muscle cell damage and inflammatory cells are observed in damaged muscle. C reactive protein (CRP) is reported to be the most abundant of the acute phase proteins and has been reported to be elevated following exercise, especially when muscle damage has occurred. Significant elevations of CRP have also been reported following several days of 2-3-hour bouts of severe physical exercise, marathon running, and a triathlon. CRP is a normal plasma protein, the circulating concentration of which rises dramatically in a cytokine-mediated response to most forms of tissue injury, infection, and inflammation, and serum CRP values are widely measured in clinical practice as an objective index of disease activity. Changes in the blood concentrations of muscle damage indicators [i.e., creatine kinase (CK)] and inflammatory biomarkers [C-reactive protein (CRP) and interleukin-6 (IL-6)] that are observed after exercise and are associated with the occurrence of DOMS can also be used to evaluate skeletal muscle recovery. C-reactive protein has been shown to increase 1000-fold in concentration in the blood in conjunction with inflammation or tissue necrosis.

Thus, the inventors evaluated the C-Reactive Protein (CRP) concentration in the muscle in an exercise-induced pain (DOMS) model of rats. Surprisingly, the compositions comprising potassium/sodium salts or complexes or chelates of 3-O-acetyl-11-keto-β-boswellic acid derived from enriched AKBA extracts from *Boswellia serrata* showed synergistic efficacy in the reduction of CRP levels in the muscles of the experimental rats.

For example, 90% AKBA (LN03) and potassium chloride (LN11) at 25 mg/kg body weight showed efficacy in reducing CRP concentration in the animals from the DOMS group, with 40.60% and 10.23% reductions in CRP respectively compared to the control animals. In comparison, the potassium salt (LN07) of LN03 containing 80% AKBA, at the same dose showed 60.75% reduction from the DOMS group animals, which is significantly higher than the CRP reductions shown by individual ingredients, suggesting a synergistic efficacy of potassium salt of 80% AKBA (LN07) in reducing CRP concentration (Table 9). Similarly, 90% AKBA (LN03) and sodium chloride (LN12) showed 40.60% and 10.64% reductions in serum CRP concentration in the animals from the DOMS group. In comparison, the corresponding sodium salt [LN08; obtained from 90% AKBA (LN03) and sodium chloride (LN12)] containing 80% AKBA showed 55.94% reduction in CRP levels in the DOMS group, which is significantly higher than the efficacy shown by the individual ingredients, suggesting a synergistic efficacy of sodium salt of 80% AKBA (LN08) in reducing CRP concentration (Table 9). These observations indicate that supplementation of LN07 or LN08 yielded synergistic benefit in reducing C-reactive protein (CRP), and hence these compositions can have better therapeutic benefits for prevention, control and/or treatment of delayed-onset of muscle soreness (DOMS) or muscle inflammation etc., compared to the individual ingredients.

The foregoing demonstrates that 3-O-acetyl-11-keto-β-boswellic acid compositions comprising 3-O-acetyl-11- keto-β-boswellic acid in combination with a metal selected from potassium or sodium as the respective metal salt or complex or chelate; shows good water solubility. Hence, these compositions may achieve desired concentration in systemic circulation for achieving the required pharmacological response. These compositions have thus shown improved efficacy to prevent, control and/or treatment of muscle pain and inflammation by reducing of LTB4 and $PGE_2$ productions than the AKBA per se. Furthermore, these compositions also showed efficacy to prevent, control and/or treatment of delayed onset muscle soreness (DOMS) by reducing CRP levels in the experimental animals. Hence, the said compositions can be useful for alleviating muscle soreness, delayed-onset of muscle soreness (DOMS), muscle tenderness, muscle pain, muscle fatigue, muscle sprain, temporary loss of muscle strength, and swelling in muscles.

Therefore, in an important embodiment, the present invention provides water-soluble 3-O-acetyl-11-keto-β-boswellic acid compositions comprising 3-O-acetyl-11-keto-β-boswellic acid in combination with a metal ion selected from potassium or sodium in the form of respective metal salts or complexes or chelates; for prevention, control and/or treatment of at least one disorder/condition selected from muscle soreness, delayed-onset of muscle soreness (DOMS), muscles tenderness, muscle pain, muscle fatigue, muscle sprain, temporary loss of muscle strength and swelling in muscles.

In another embodiment, the present invention provides a process for the preparation of the compositions comprising 3-O-acetyl-11-keto-β-boswellic acid in combination with a metal ion selected from potassium or sodium in the form of respective metal salts or complexes or chelates; wherein the process comprising the following steps;

(i) dissolving 3-O-acetyl-11-keto-β-boswellic acid in a suitable solvent;
(ii) treating the solution with a metal compound;
(iii) filtering the solution; and
(iv) evaporating the solvent and drying the residue to obtain the corresponding metal salt or chelate or complex of 3-O-acetyl-11-keto-β-boswellic acid.

In other embodiment, the present invention provides methods of prevention, control and/or treatment of at least one disorder/condition selected from muscle soreness, delayed-onset of muscle soreness (DOMS), muscles tenderness, muscle pain, muscle fatigue, muscle sprain, temporary loss of muscle strength and swelling in muscles in humans, wherein the method comprises supplementing said human with a water-soluble 3-O-acetyl-11-keto-β-boswellic acid compositions comprising 3-O-acetyl-11-keto-β-boswellic acid in combination with a metal selected from potassium or sodium in the form of respective metal salt or complex or chelate; and optionally containing at least one component selected from pharmaceutically or nutraceutically or dietetically acceptable excipients, carriers or diluents.

In other embodiment, the present invention provides use of water-soluble 3-O-acetyl-11-keto-β-boswellic acid compositions comprising 3-O-acetyl-11-keto-β-boswellic acid in combination with a metal selected from potassium or sodium in the form of respective metal salt or complex or chelate; and optionally containing at least one component selected from pharmaceutically or nutraceutically or dietetically acceptable excipients, carriers or diluents; for prevention, control and/or treatment of at least one disorder/condition selected from muscle soreness, delayed-onset of muscle soreness (DOMS), muscles tenderness, muscle pain, muscle fatigue, muscle sprain, temporary loss of muscle strength and swelling in muscles.

In another embodiment, the composition(s) of the present invention may be formulated into a dosage form selected from dry powder form, liquid form, beverage, food product, dietary supplement, or any suitable form such as a tablet, a capsule, or a soft chewable or gummy bear.

In another embodiment of the invention, the composition(s) as disclosed above can be formulated into nutritional/dietary supplements that can be contemplated/made into the dosage form of healthy foods, or food for specified health uses such as solid food like chocolate or nutritional bars, semisolid food like cream or jam, or gel and also beverage and the like, such as refreshing beverage, instant beverage, functional beverages for sports athletes, exercising and muscle building for individuals, lactic acid bacteria beverage, drop, candy, chewing gum, gummy candy, yogurt, ice cream, pudding, soft adzuki bean jelly, jelly, cookie, tea, soft drink, juice, milk, coffee, cereal, snack bar and the like.

In another embodiment, the composition(s) of the present invention can be delivered in the form of controlled-release tablets, using controlled release polymer-based coatings by techniques including nanotechnology, microencapsulation, colloidal carrier systems and other drug delivery systems for obtaining the desired therapeutic benefit.

Those of ordinary skilled in the art will appreciate that changes could be made to the embodiments described above without departing from the broad inventive concept thereof. It is understood, therefore, that this invention is not limited to the particular embodiments or examples disclosed herein, but is intended to cover modifications within the objectives and scope of the present invention as defined in the specification. The presented examples illustrate the invention, but they should not be considered to limit the scope of the invention in any way.

EXAMPLES

Enrichment of 3-O-acetyl-11-keto-β-boswellic acid (AKBA) from boswellic acid mixture is a known art. Various grades of AKBA such as 40% AKBA (LN01), 60% AKBA (LN02), 90% AKBA (LN03) and 99% AKBA (LN04) was prepared from boswellic acids mixture obtained from *Boswellia serrata* gum resin by known enrichment techniques, such as column chromatography and or crystallization in a suitable solvent. Some of these AKBA enriched compounds are commercially available and they can also be used for the preparation of the compositions. These different grades of products were analyzed for AKBA by the analytical HPLC method.

Example 1: Preparation of Potassium Salt of 90% AKBA (LN05)

To a solution of 99.24% AKBA (LN04, 2.0 g, 3.87 mmol) in methanol (60 mL) was added potassium hydroxide powder (85% pure, 260 mg, 3.94 mmol) at RT and stirred for 2 h. The solution was filtered, and the solvent was evaporated under reduced pressure. The residue was dried under vacuum to give the product as a white solid (LN05, 2.1 g).

Example 2: Preparation of Sodium Salt of 90% AKBA (LN06)

To a solution of 99.24% AKBA (LN04, 2.0 g, 3.87 mmol) in methanol (60 mL) was added sodium hydroxide powder (98% pure, 160 mg, 3.92 mmol) at RT and stirred for 2 h.

The solution was filtered, and the solvent was evaporated under reduced pressure. The residue was dried under vacuum to give the product as a white color solid (LN06, 2.05 g).

Example 3: Preparation of Potassium Salt of 80% AKBA (LN07)

To a solution of 90.66% AKBA (LN03, 3.0 g, 5.31 mmol) in methanol (90 mL) was added potassium hydroxide powder (85% pure, 380 mg, 5.76 mmol) at RT and stirred for 2 h. The solution was filtered, and the solvent was evaporated under reduced pressure. The residue was dried under vacuum to give the product as an off-white color solid (LN07, 3.1 g).

Example 4: Preparation of Sodium Salt of 80% AKBA (LN08)

To a solution of 90.66% AKBA (LN03, 3.0 g, 5.31 mmol) in methanol (90 mL) was added sodium hydroxide powder (98% pure, 380 mg, 5.63 mmol) at rt and stirred for 2 h. The solution was filtered, and the solvent was evaporated under reduced pressure. The residue was dried under vacuum to give the product as an off-white color solid (LN08, 3.2 g).

Example 5: Preparation of Potassium Salt of 50% AKBA (LN09)

To a solution of 60.2% AKBA (LN02, 3.0 g, 3.52 mmol) in methanol (90 mL) was added potassium hydroxide powder (85% pure, 426 mg, 6.46 mmol) at RT and stirred for 2 h. The solution was filtered, and the solvent was evaporated under reduced pressure. The residue was dried under vacuum to give the product as a light brown color solid (LN09, 3.1 g).

Example 6: Preparation of Potassium Salt of 30% AKBA (LN10)

To a solution of 41.4% AKBA (LN01, 3.0 g, 2.42 mmol) in methanol (90 mL) was added potassium hydroxide powder (85% pure, 425 mg, 6.45 mmol) at RT and stirred for 2 h. The solution was filtered, and the solvent was evaporated under reduced pressure. The residue was dried under vacuum to give the product as a light brown color solid (LN10, 3.1 g).

Example 7: Standardization of Potassium or Sodium Salts of AKBA

The potassium or sodium salts of AKBA disclosed above were analyzed for AKBA by analytical HPLC. The concentrations of K and Na were analyzed by flame photometry, and the results are summarized in Table 1.

TABLE 1

Analysis data of potassium or sodium salts of AKBA

| Compound | AKBA assay by HPLC | K/Na assay by Flame photometry |
|---|---|---|
| LN05 | 90.85% | K: 6.46% |
| LN06 | 90.33% | Na: 4.56% |
| LN07 | 80.77% | K: 6.55% |
| LN08 | 82.16% | Na: 4.68% |
| LN09 | 50.08% | K: 7.30% |
| LN10 | 36.18% | K: 5.55% |

Example 8: Solubility and pH of Potassium or Sodium Salts of AKBA

These potassium or sodium salts of AKBA were evaluated for their solubility in water and determined their pH. The results are summarized in Table-2.

TABLE 2

Solubility data of potassium or sodium salts of AKBA

| Compound | Product description | Solubility of 1.0 g of product in water | pH (1% solution) |
|---|---|---|---|
| LN04 | 99% AKBA | >1000 mL | 6.64 |
| LN03 | 90% AKBA | >1000 mL | 6.63 |
| LN05 | K salt of 90% AKBA | 140 mL | 9.24 |
| LN06 | Na salt of 90% AKBA | 80 mL | 9.27 |
| LN07 | K salt of 80% AKBA | 60 mL | 9.21 |
| LN08 | Na salt of 80% AKBA | 50 mL | 8.74 |
| LN09 | K salt of 50% AKBA | 40 mL | 8.84 |

Example 9: Preparation of Tablet Contain Potassium Salt of 800% AKBA

| Ingredient | Wt for 50 mg dose of the product |
|---|---|
| K salt of 80% AKBA (LN07) | 50 mg |
| Microcrystalline cellulose | 18 mg |
| Lactose anhydrous | 38.5 mg |
| Sodium starch glycolate | 11.5 mg |
| Pre-gelatinized starch | 3.0 mg |
| Aerosil (colloidal silicon dioxide) | 2.0 mg |
| Magnesium stearate | 2.0 mg |
| Total | 125 mg |

Tablets of potassium salt of 80% AKBA were prepared by direct compression method using 10 Station Cadmach Rotary Compression Machine. Suitable quantities of each ingredient for a batch size of 500 tablets were weighed. The blending of ingredients was done by geometric dilution method. Suitable quantities of pre-gelatinized starch, sodium starch glycolate were transferred into polybag and mixed for 2 minutes. To this blend, required quantity of lactose anhydrous, microcrystalline cellulose were added and mixed for further 2 minutes. To this ingredient blend, suitable quantity of K salt of 80% AKBA was added and mixed uniformly for 4 minutes. Finally, aerosil and magnesium stearate were added and mixed for further 2 minutes. After complete mixing, the blend was passed through sieve #40. The blend was subjected to compression. The tablets were compressed using 6.5 mm round, Biconcave punches with a total tablet weight of 125±10 mg for each tablet.

Example 10: Assay for Leukotriene $B_4$ ($LTB_4$) Inhibition

Human blood was collected from healthy volunteers from a peripheral vein in the presence of 2 mM EDTA. Plasma was separated by centrifugation at 1000 rpm for 10 minutes, and the residual cell pellet was resuspended in RPMI medium supplemented with 10% FBS and 2 mM EDTA. Thirty milliliters of blood cell suspension was carefully overlayed onto 15 mL of Ficoll/Lymphoprep in a 50 mL falcon tube in the dark, and the tube was centrifuged at 350×g for 30 minutes without using the brake. After removing the peripheral blood mononuclear cells (PBMC) and Ficoll/Lymphoprep, the settled red blood cell (RBC) layer containing granulocytes was treated with ACK lysis buffer (Gibco Cat #A10492-01) to lyse the RBC. After centrifugation at 1200 rpm for 10 minutes, the resulting cell pellet of polymorphonuclear leukocytes (PMNs) was resuspended in RPMI containing 1% newborn calf serum (NBCS). These cells were seeded in a 96-well plate at a density of 50,000 cells/well and treated with different concentrations of the test samples. Cells with 0.2% DMSO served as vehicle control. The plate was incubated in a $CO_2$ incubator at 37° C. for 2 hrs. Finally, the cells treated with test samples were induced with 10 μM A23187 for 10 minutes at 37° C. in a $CO_2$ incubator. The cells treated with only A23187 served as induction control. The plate was centrifuged at 1200 rpm for 5 minutes, and 120 μL cell-free supernatants were collected. Quantitation of LTB4 was performed using an ELISA kit (R&D Systems, Cat #SKGE006B) following the manufacturer's instructions. Absorbance was measured at 450 nm with a correction wavelength of 570 nm in a plate reader (Spectramax2e, Molecular Devices, USA). The reduction of LTB4 production was calculated using the following formula.

% reduction of $LTB_4$=[(Normalized Conc. of $LTB_4$ in Induction)−(Normalized Conc. of $LTB_4$ in Test sample)]/(Normalized Conc. of LTB4 in Induction)×100

The results are presented in tables: 3-5.

TABLE 3

Reduction of LTB4 production by K & Na salt of 90% AKBA

| Compound | Product | % reduction of LTB4 1.0 μg/mL | % reduction of LTB4 2.5 μg/mL |
|---|---|---|---|
| LN04 | 99% AKBA | 16.03 | 28.71 |
| LN05 | K salt of 90% AKBA | 21.95 | 57.57 |
| LN06 | Na salt of 90% AKBA | 20.16 | 47.87 |

TABLE 4

Reduction of LTB4 production by K & Na salt of 80% AKBA

| Compound | Product | % reduction of LTB4 1.0 μg/mL | % reduction of LTB4 2.5 μg/mL |
|---|---|---|---|
| LN03 | 90% AKBA | 16.72 | 26.83 |
| LN07 | K salt of 80% AKBA | 20.26 | 55.85 |
| LN08 | Na salt of 80% AKBA | 21.66 | 46.10 |

TABLE 5

Reduction of LTB4 production by K salt of 50% and 30% AKBA

| Compound | Product | % reduction of LTB4 1.0 μg/mL | % reduction of LTB4 2.5 μg/mL |
|---|---|---|---|
| LN02 | 60% AKBA | 10.85 | 22.05 |
| LN09 | K salt of 50% AKBA | 15.98 | 45.70 |
| LN01 | 40% AKBA | 9.57 | 18.40 |
| LN10 | K salt of 30% AKBA | 14.89 | 42.09 |

Example 11: Assay for Prostaglandin $E_2$ ($PGE_2$) Inhibition

Human blood was collected from healthy volunteers from a peripheral vein with a syringe containing EDTA at a final concentration of 2 mM. Plasma was separated by centrifugation at 1000 rpm for 10 minutes, and the residual blood was diluted with RPMI medium supplemented with 10% FBS and 2 mM EDTA in a ratio of 1:3. Thirty milliliters of blood was carefully layered onto the 15 mL of Ficoll/Lymphoprep in a 50 mL falcon tube, and tubes were centrifuged at 350×g for 30 minutes at an acceleration of 9 without using the brake. Buffy coat (interface between medium and Ficoll) containing peripheral blood mononuclear cells (PBMC) was collected carefully in 25 mL of cold 1× phosphate-buffered saline (PBS) and centrifuged at 1200 rpm for 10 minutes. Residual RBCs found in PBMCs pellet were removed by treating with ACK lysis buffer (Gibco Cat #A10492-01) and washed with fresh 1×PBS. PBMC were seeded in a 96-well plate with a density of $0.1\times10^6$ cells/well and treated with different concentrations of test samples. Cells with 0.2% DMSO served as vehicle control. The plate was incubated in a $CO_2$ incubator at 37° C. for 2 hrs. Finally, cells were induced with LPS (10 ng/mL final concentration) for 4 hours except for vehicle control by keeping the plate at 37° C. in a $CO_2$ incubator. The plate was centrifuged at 1200 rpm for 5 minutes, and 120 μL cell-free supernatants were collected. Quantitation of $PGE_2$ was performed using an ELISA kit (Cayman Chemicals Cat #514010) according to the manufacturer's instructions. Absorbance was measured at 412 nm in a kinetic mode for 30 minutes in a microplate reader (Spectramax2e, Molecular Devices, USA). Percent Inhibition of $PGE_2$ was calculated using the following formula.

% Inhibition of $PGE_2$=(Normalized conc. of $PGE_2$ in Induction)−(Normalized conc. of $PGE_2$ in Test sample)/×100

(Normalized conc. of $PGE_2$ in Induction)

The normalized $PGE_2$ concentration in the LPS induced or the treated wells were obtained from deducting the values in the test samples from the vehicle control samples.

The results are presented in tables: 6-8.

TABLE 6

$PGE_2$ inhibitory activity of K & Na salt of 90% AKBA

| Compound | Product | % Inhibition of $PGE_2$ 1.0 μg/mL | % Inhibition of $PGE_2$ 2.5 μg/mL |
|---|---|---|---|
| LN04 | 99% AKBA | 17.22 | 20.03 |
| LN05 | K salt of 90% AKBA | 24.42 | 42.29 |
| LN06 | Na salt of 90% AKBA | 25.64 | 41.23 |

TABLE 7

| PGE$_2$ inhibitory activity of K & Na salt of 80% AKBA | | | |
|---|---|---|---|
| | | % Inhibition of PGE$_2$ | |
| Compound | Product | 1.0 μg/mL | 2.5 μg/mL |
| LN03 | 90% AKBA | 15.02 | 26.28 |
| LN07 | K salt of 80% AKBA | 26.50 | 49.08 |
| LN08 | Na salt of 80% AKBA | 25.61 | 47.56 |

TABLE 8

| PGE$_2$ inhibitory activity of K & Na salt of 50% and 30% AKBA | | | |
|---|---|---|---|
| | | % Inhibition of PGE$_2$ | |
| Compound | Product | 1.0 μg/mL | 2.5 μg/mL |
| LN02 | 60% AKBA | 12.84 | 21.65 |
| LN09 | K salt of 50% AKBA | 16.84 | 30.76 |
| LN01 | 40% AKBA | 10.75 | 18.09 |
| LN10 | K salt of 30% AKBA | 14.97 | 26.41 |

Example 12: Assay for Reduction of C-Reactive Protein (CRP)

On day 1 of the study, male Sprague Dawley rats (8-12 weeks) were randomized into seven groups, each group contained seven animals. Basal readings (Paw Withdrawal Threshold) of mechanical hyperalgesia (Electronic von Frey) were obtained. Animals were dosed with either 25 mg/kg of the test items or vehicle (0.5% CMC-Na) for seven days. On day 5, Delayed Onset of Muscle Soreness (DOMS) was induced by introducing the animals to downhill treadmill running task (rate, 15 m/min; time, 5 min; incline, −20° followed by a 1-min rest, repeated 18 times) for 90 min or till exhaustion. Paw Withdrawal Threshold (PWT) was measured at 1 h, 4 h, 24 h (day 6) and 48 h (day 7) post to eccentric exercise and the exploratory behavior measurements were taken at 1 h and 4 h post to DOMS induction. Terminal necropsy was performed after euthanizing the animals under CO2 asphyxiation.

Small pieces of the extensor digitorum longus (EDL) muscles were macerated in liquid nitrogen (LN2) and homogenized in a tissue lysis buffer [50 mM Tris-HCl (pH 7.4), 150 mM NaCl, 5 mM EDTA, 0.5% sodium dodecyl sulfate (SDS), 1% deoxycholate, 0.1% Triton X-100, 1% Nonidet P-40 (NP-40), 0.05% mercaptoethanol, 10 mg/ml PMSF, 0.5 mg/ml leupeptin, 0.2 mg/ml aprotinin, and 1 mM $Na_3VO_4$]. The homogenate was centrifuged at 18928 g for 25 min at 4° C., and the supernatant was collected. Protein concentrations of the tissue lysates were determined using BCA protein assay kit (Thermo Fisher, Rockford, IL). C-reactive protein (CRP) concentrations in the muscle tissue lysates were determined using a commercial kit (Rat CRP/C-Reactive Protein ELISA Kit, Sigma, Cat #RAB0097) following the manufacturer's instructions, where the samples were diluted with assay buffer (1:10000) and performed the assay. The amount of CRP present in the tissue lysates was calculated and expressed as nanogram (ng) per milligram of protein. The reduction of CRP concentration in the muscle samples in the treated groups was calculated using the following formula.

$$\% \text{ reduction of } CRP = \frac{[(DOMS \text{ control} - \text{normal control}) - (\text{treatment} - \text{normal control})] \times 100}{(DOMS \text{ control} - \text{normal control})}$$

The results were presented in table-9.

TABLE 9

| Reduction of C-reactive protein (CRP) concentration | | | |
|---|---|---|---|
| Group | Description of product | Mean CRP conc. (ng/mg of protein) | % reduction of CRP from normal control |
| Normal control | — | 40.47 | — |
| DOMS | — | 82.51 | — |
| LN03 | 90% AKBA | 65.44 | 40.60 |
| LN11 | KCl | 78.21 | 10.23 |
| LN07 | K salt of 80% AKBA | 56.97 | 60.75 |
| LN12 | NaCl | 78.04 | 10.64 |
| LN08 | Na salt of 80% AKBA | 58.99 | 55.94 |

Note:
Higher reduction of CRP is better efficacy

We claim:

1. A water-soluble 3-O-acetyl-11-keto-β-boswellic acid composition comprising 3-O-acetyl-11-keto-β-boswellic acid in combination with a metal ion selected from potassium or sodium in the form of a respective metal salt or complex or chelate; for the control and/or treatment of at least one disorder/condition selected from muscle soreness, delayed-onset of muscle soreness (DOMS), muscles tenderness, muscle pain, muscle fatigue, muscle sprain, temporary loss of muscle strength and swelling in muscles.

2. The water-soluble 3-O-acetyl-11-keto-β-boswellic acid composition as claimed in claim 1, wherein the 3-O-acetyl-11-keto-β-boswellic acid is in a concentration range of 30-95% by weight of the composition and the potassium or sodium is in a concentration range of 3.0-10% by weight of the composition.

3. The water-soluble 3-O-acetyl-11-keto-β-boswellic acid composition as claimed in claim 1, wherein the compositions contains at least one component selected from a pharmaceutically or nutraceutically or dietetically acceptable excipient, carriers or diluents.

4. The water-soluble 3-O-acetyl-11-keto-β-boswellic acid composition as claimed in claim 3, wherein the pharmaceutically or nutraceutically or dietetically acceptable excipient, carrier or diluents is selected from a monosaccharide, a disaccharide, a polycarbohydrate, a dextrin, a polyhydric alcohol or sugar alcohol, a cellulose based derivative, a silicate, a metallic stearate, an organic acid, a fatty acid ester, an ester of polysorbate, a natural gum, a vitamin B group, a nicotinamide, a calcium pantothenate, an amino acid, a protein, an organic metal salt, a natural pigments, a flavor, a class I preservative, a class II preservative, an aqueous, alcoholic, hydro-alcoholic, organic solution of above listed ingredients alone or in combination.

5. The water-soluble 3-O-acetyl-11-keto-β-boswellic acid composition as claimed in claim 1, wherein the composition is formulated into a dosage form selected from dry powder form, liquid form, beverage, food product, dietary supplement, a tablet, a capsule, a soft chewable tablet, or a gummy bear.

6. The water-soluble 3-O-acetyl-11-keto-β-boswellic acid composition as claimed in claim 1, wherein the composition is formulated into a nutritional/dietary supplements that can be contemplated/made into the dosage form of a healthy food, or food for a specified health use, or gel or beverage.

7. The water-soluble 3-O-acetyl-11-keto-β-boswellic acid composition as claimed in claim 1, wherein the composition is formulated into a controlled release tablet using a controlled release polymer-based coating by a technique including nanotechnology, microencapsulation, colloidal earner system or other drug delivery system for obtaining the desired therapeutic benefit.

8. A process for the preparation of a water-soluble 3-O-acetyl-11-keto-β-boswellic acid compositions comprising 3-O-acetyl-11-keto-β-boswellic acid in combination with a metal ion selected from potassium or sodium in the form of respective metal salt or complex or chelate; the process comprising the following steps;

(i) dissolving 3-O-acetyl-11-keto-β-boswellic acid in a suitable solvent;

(ii) treating the solution with a metal compound;

(iii) filtering the solution; and (iv) evaporating the solvent and drying the residue to obtain the corresponding metal salt or chelate or complex of 3-O-acetyl-11-keto-β-boswellic acid.

9. The process for the preparation of the water-soluble 3-O-acetyl-11-keto-β-boswellic acid composition as claimed in claim 8, wherein the suitable solvent is selected from a C1-C5 alcohol or a mixture thereof.

10. The process for the preparation of the water-soluble 3-O-acetyl-11-keto-β-boswellic acid composition as claimed in claim 8, wherein the metal compound is selected from a metal salt, a metal oxide, a metal hydroxide, or a metal carbonate of a metal selected from potassium or sodium.

11. A method for control and/or treatment of at least one disorder/condition selected from muscle soreness, delayed-onset of muscle soreness (DOMS), muscles tenderness, muscle pain, muscle fatigue, muscle sprain, temporary loss of muscle strength and swelling in muscles in humans, wherein the method comprises supplementing said human with a water soluble 3-O-acetyl-11-keto-β-boswellic acid compositions comprising 3-O-acetyl-11-keto-β-boswellic acid in combination with a metal ion selected from potassium or sodium in the form of respective metal salt or complex or chelate; and optionally containing at least one component selected from pharmaceutically or nutraceutically or dietetically acceptable excipients, carriers or diluents.

12. The water-soluble 3-O-acetyl-11-keto-β-boswellic acid composition as claimed in claim 2, wherein the composition is formulated into a dosage form selected from dry powder form, liquid form, beverage, food product, dietary supplement, a tablet, a capsule, a soft chewable tablet, or a gummy bear.

13. The water-soluble 3-O-acetyl-11-keto-β-boswellic acid composition as claimed in claim 3, wherein the composition is formulated into a dosage form selected from dry powder form, liquid form, beverage, food product, dietary supplement, a tablet, a capsule, a soft chewable tablet, or a gummy bear.

14. The water-soluble 3-O-acetyl-11-keto-β-boswellic acid composition as claimed in claim 4, wherein the composition is formulated into a dosage form selected from dry powder form, liquid form, beverage, food product, dietary supplement, as a tablet, a capsule, a soft chewable tablet, or a gummy bear.

15. The water-soluble 3-O-acetyl-11-keto-β-boswellic acid composition as claimed in claim 2, wherein the composition is formulated into nutritional/dietary supplements that can be contemplated/made into the dosage form of healthy foods, or food for specified health use or gel or beverage.

16. The water-soluble 3-O-acetyl-11-keto-β-boswellic acid composition as claimed in claim 3, wherein the composition is formulated into nutritional/dietary supplements that can be contemplated/made into the dosage form of healthy foods, or food for specified health use, or gel or beverage.

17. The water-soluble 3-O-acetyl-11-keto-β-boswellic acid composition as claimed in claim 4, wherein the composition is formulated into nutritional/dietary supplements that can be contemplated/made into the dosage form of healthy foods, or food for specified health use, or gel or beverage.

18. The water-soluble 3-O-acetyl-11-keto-β-boswellic acid composition as claimed in claim 5, wherein the composition is formulated into nutritional/dietary supplements that can be contemplated/made into the dosage form of healthy foods, or food for specified health use, or gel or beverage.

19. The water-soluble 3-O-acetyl-11-keto-β-boswellic acid composition as claimed in claim 2, where in the composition is formulated into controlled release tablets, using controlled release polymer-based coatings by the techniques including nanotechnology, microencapsulation, colloidal earner systems and other drug delivery systems for obtaining the desired therapeutic benefit.

20. The water-soluble 3-O-acetyl-11-keto-β-boswellic acid composition as claimed in claim 3, where in the composition is formulated into controlled release tablets, using controlled release polymer-based coatings by the techniques including nanotechnology, microencapsulation, colloidal earner systems and other drug delivery systems for obtaining the desired therapeutic benefit.

21. The water-soluble 3-O-acetyl-11-keto-β-boswellic acid composition as claimed in claim 4, where in the composition is formulated into controlled release tablets, using controlled release polymer-based coatings by the techniques including nanotechnology, microencapsulation, colloidal earner systems and other drug delivery systems for obtaining the desired therapeutic benefit.

22. The water-soluble 3-O-acetyl-11-keto-β-boswellic acid composition as claimed in claim 5, where in the composition is formulated into controlled release tablets, using controlled release polymer-based coatings by the techniques including nanotechnology, microencapsulation, colloidal earner systems and other drug delivery systems for obtaining the desired therapeutic benefit.

23. The water-soluble 3-O-acetyl-11-keto-β-boswellic acid composition as claimed in claim 6, where in the composition is formulated into controlled release tablets, using controlled release polymer-based coatings by the techniques including nanotechnology, microencapsulation, colloidal earner systems and other drug delivery systems for obtaining the desired therapeutic benefit.

* * * * *